US008560050B2

(12) United States Patent
Martin et al.

(10) Patent No.: US 8,560,050 B2
(45) Date of Patent: Oct. 15, 2013

(54) METHOD AND DEVICE FOR IMAGING OBJECTS

(75) Inventors: Diana Martin, Herzogenaurach (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 845 days.

(21) Appl. No.: 12/071,454

(22) Filed: Feb. 21, 2008

(65) Prior Publication Data

US 2008/0214929 A1 Sep. 4, 2008

(30) Foreign Application Priority Data

Feb. 26, 2007 (DE) .......................... 10 2007 009 183

(51) Int. Cl.
*A61B 5/055* (2006.01)

(52) U.S. Cl.
USPC ........... 600/411; 600/407; 600/410; 600/426; 600/429; 600/437; 600/438; 382/128; 382/130; 382/131; 382/294

(58) Field of Classification Search
USPC .......... 600/407, 408, 410, 426, 429; 382/128, 382/130, 131, 294
See application file for complete search history.

(56) References Cited

U.S. PATENT DOCUMENTS

| | | | |
|---|---|---|---|
| 5,613,013 A * | 3/1997 | Schuette ....................... | 382/124 |
| 6,266,453 B1 * | 7/2001 | Hibbard et al. ................ | 382/294 |
| 6,775,404 B1 * | 8/2004 | Pagoulatos et al. ........... | 382/154 |
| 7,050,087 B2 * | 5/2006 | Harari et al. .................... | 348/80 |
| 7,110,587 B1 * | 9/2006 | Natanzon et al. ............. | 382/131 |
| 7,323,874 B2 * | 1/2008 | Krieg et al. .................... | 324/318 |
| 7,412,280 B2 | 8/2008 | Hertel et al. | |
| 7,764,984 B2 * | 7/2010 | Desmedt et al. .............. | 600/424 |
| 8,089,279 B2 | 1/2012 | Martin et al. | |
| 8,199,168 B2 | 6/2012 | Virtue | |
| 2003/0097055 A1 * | 5/2003 | Yanof et al. ................... | 600/407 |
| 2004/0015327 A1 * | 1/2004 | Sachdeva et al. ............. | 702/167 |
| 2005/0041772 A1 | 2/2005 | Nishide | |
| 2006/0058647 A1 * | 3/2006 | Strommer et al. ............ | 600/434 |

(Continued)

FOREIGN PATENT DOCUMENTS

| | | |
|---|---|---|
| CN | 1582854 | 2/2005 |
| DE | 102005015071 | 10/2006 |

(Continued)

OTHER PUBLICATIONS

Office Applicant encloses a copy of the German Office Action issued on Oct. 23, 2007.

(Continued)

*Primary Examiner* — Baisakhi Roy
(74) *Attorney, Agent, or Firm* — Harness, Dickey & Pierce, P.L.C.

(57) ABSTRACT

A method for imaging objects is disclosed. In at least one embodiment, the method includes using a first and a second imaging method which differ at least in regard to the spatial resolution or sensitivity. Furthermore, in at least one embodiment, the method includes generating an overview image at least by the first or the second imaging method; simultaneously planning the measurement of the first and the second imaging method on the basis of the overview image; and simultaneously conducting the planned measurements of the first and the second imaging method. A device which conducts at least one embodiment of the method is also disclosed.

13 Claims, 1 Drawing Sheet

(56) References Cited

U.S. PATENT DOCUMENTS

| | | |
|---|---|---|
| 2006/0250133 A1 | 11/2006 | Krieg et al. |
| 2008/0125846 A1* | 5/2008 | Battle et al. ................... 623/1.11 |
| 2008/0146914 A1 | 6/2008 | Polzin et al. |
| 2008/0287777 A1* | 11/2008 | Li et al. .......................... 600/424 |

FOREIGN PATENT DOCUMENTS

| | | |
|---|---|---|
| JP | 2005021689 | 1/2005 |
| JP | 2006280929 | 10/2006 |
| JP | 2007136186 | 6/2007 |
| JP | 2008149147 | 7/2008 |
| JP | 2008155026 | 7/2008 |
| WO | WO 2006071922 A2 | 7/2006 |

OTHER PUBLICATIONS

Japanese Office Action for Application No. 2008-037441, dated Sep. 13, 2012, and English translation thereof.

* cited by examiner

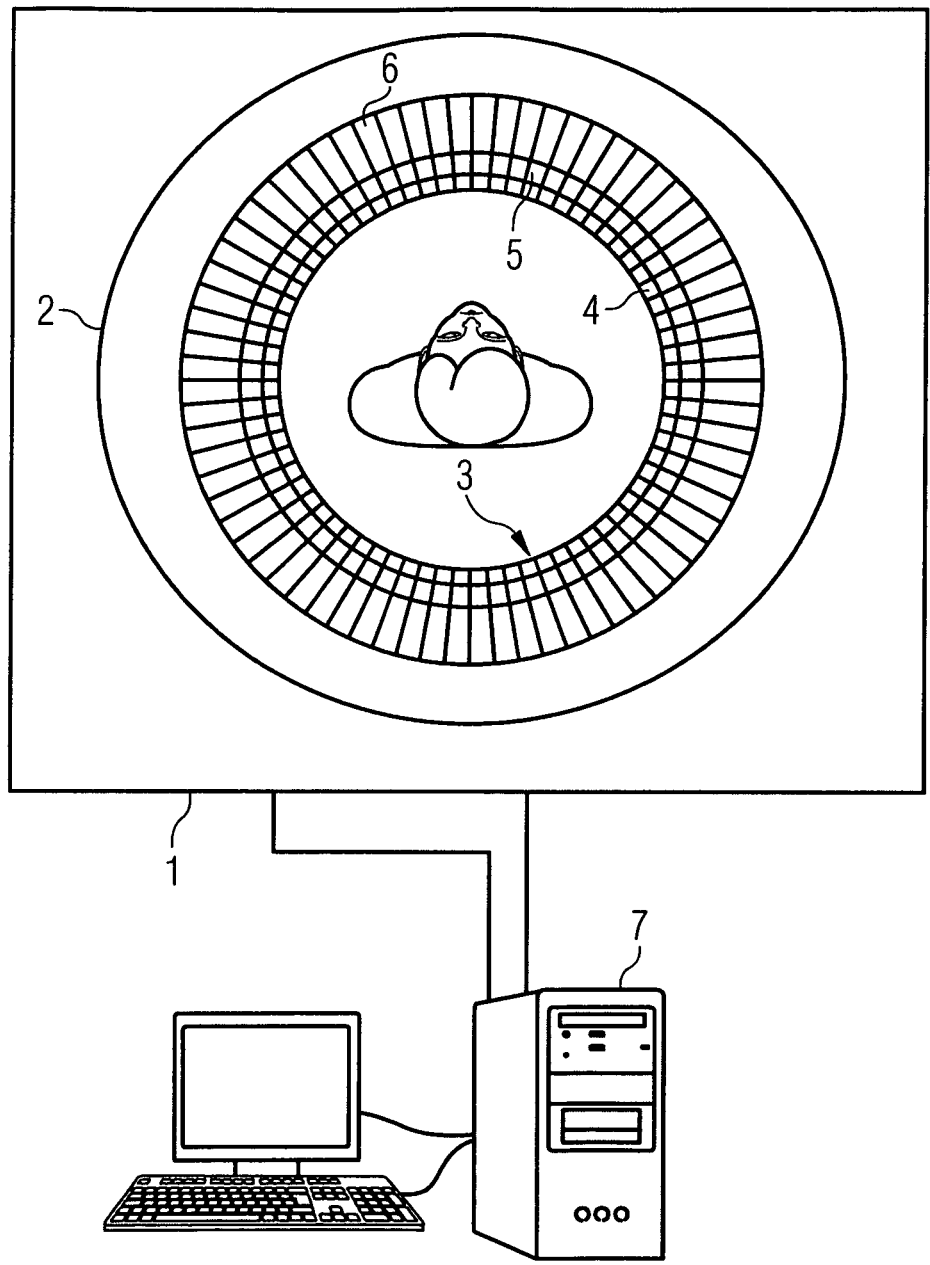

METHOD AND DEVICE FOR IMAGING OBJECTS

PRIORITY STATEMENT

The present application hereby claims priority under 35 U.S.C. §119 on German patent application number DE 10 2007 009 183.6 filed Feb. 26, 2007, the entire contents of which is hereby incorporated herein by reference.

FIELD

Embodiments of the present invention generally relate to a method and/or a device for imaging objects using a first and a second imaging method which differ at least in regard to the spatial resolution or sensitivity. In at least one embodiment, the method and/or the device for imaging are particularly suitable for medical interventions.

BACKGROUND

Recently, so-called "hybrid modalities", such as PET/CT, SPECT/CT, MR/PET and MR/SPECT, have become increasingly important in medical imaging. In this case,
PET stands for positron emission tomography,
CT stands for computed tomography,
SPECT stands for single photon emission computed tomography, and
MR stands for magnetic resonance tomography.

Advantageously, these combinations combine a modality having a high spatial resolution (in particular MR or CT) with a modality having high sensitivity (in particular, nuclear medicine, abbreviated NM in the following, such as SPECT or PET).

Already the appropriate preparation and conduct of the examination is important for an optimal diagnostic evaluation of data sets acquired in such a way.

Already established methods utilize a sequential recording of the two modalities. This also results in a sequential progression in the planning of the acquisition. For example, CT measurements and PET measurements are planned following one another.

However, for simultaneous acquisition of two modalities, as is possible for example in the case of the MR/PET hybrid modality, an option is desirable, which both increases usability and optimizes the quality of the results data.

SUMMARY

In at least one embodiment of the present invention, a method and/or a device for imaging objects is provided, using a first and a second imaging method, which differ at least in regard to the spatial resolution or sensitivity, with the method and the device allowing a simultaneous acquisition of two modalities without detrimental effects to the usability and the quality of the results data.

At least one embodiment of the inventive method for imaging objects uses a first and a second imaging method which differ at least in regard to the spatial resolution or sensitivity. Furthermore, at least one embodiment of the inventive method for imaging includes steps for the generation of an overview image at least by the first or the second imaging method; for the simultaneous planning of the measurements of the first and the second imaging method on the basis of the overview image; and for the simultaneous conduct of the planned measurements of the first and the second imaging method.

Advantageously, during the simultaneous planning of the measurements of the first and the second imaging method on the basis of the overview image, a user interface is used in which a common coordinate system for the first and the second imaging method is defined.

Since the measurements of the two modalities can be imaged almost perfectly relative to one another, both the operational convenience for the user and the quality of the results data are thus increased in an advantageous manner.

BRIEF DESCRIPTION OF THE DRAWINGS

An example embodiment of the invention is now described with reference to the attached FIGURE.

The FIGURE shows a device 1 for imaging according to an embodiment of the present invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the FIGURES.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes,"

and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The device 1 is a combined MR/NM unit, in this example an MR/PET unit (an MR/SPECT unit would also be possible), which allows a simultaneous and isocentric measurement of the MR and NM data.

The device 1 has a known MR tube 2.

A plurality of PET detection units 3 are arranged coaxially within the MR tube 2, lying in pairs opposite one another about the longitudinal direction. Preferably, the PET detection units 3 comprise an APD photodiode array 5 with an array of LSO crystals 4 connected upstream thereof, and an electrical amplifier circuit (PMT) 6. However, the invention is not restricted to PET detection units 3 with the APD photodiode array 5 and the array of LSO crystals 4 connected upstream thereof; rather, different types of photodiodes, crystals and devices can similarly also be used for detection.

The MR tube 2 defines a cylindrical first field of view along its longitudinal direction. The multiplicity of PET detection units 3 defines a cylindrical second field of view along the longitudinal direction z. The second field of view of the PET detection units 3 preferably essentially corresponds to the first field of view of the MR tube 2. For example, this is implemented by correspondingly adapting the arrangement density of the PET detection units 3 along the longitudinal direction z.

The image processing is conducted by a computer 7.

A method for imaging is now described by way of example which is conducted by the device 1 shown for imaging.

Firstly, an overview image of an object is generated, preferably by the MR method at low resolution. Such overview images are also referred to as scouts.

The planning for the actual MR and NM measurements is then conducted on the basis of the overview image. The planning for the MR and NM measurements is conducted at the same time, that is to say synchronously and in each case on the basis of the already generated overview image.

The planning includes, inter alia, the widely known setting of the parameters required for the MR and NM measurements, such as the fields of view (FoV), the layer thicknesses and layer spacings, the measurement volume, the weighting of the MR sequences (T1, T2), etc.

In order to conduct the simultaneous planning of the MR and NM measurements, the computer 7 provides a suitable user interface which defines a common coordinate system for the MR and NM measurements. The planning of the combined measurement is conducted in synchronized representation on the user interface.

The planning of the MR and NM measurements can also be conducted on images of the combined modalities, for example not only on the basis of MR data, but also on the basis of PET data or fused data. In this case, a further overview image would have to be generated by the NM method.

After planning, the planned MR and NM measurements are conducted simultaneously.

The fields of view (FoV) of the measurements conducted simultaneously are in each case imaged on the same planning images at the same time, and can, for example, be jointly or separately graphically changed/adapted. The visualization can be switched over by user control, for example to show only the MR measurement, only the PET measurement or a combined display. For this purpose, the NM reconstruction volume can also be directly adapted graphically, for example to the MR examination volume.

In the case of examinations which examine a relatively large measuring area, such as whole body recordings, it is possible to visualize all levels and/or the complete examination volume, even if it is subdivided into a number of measurement steps. In this case, which partial steps of the two modalities are being conducted simultaneously is always visualized. For example, this can be conducted by way of color coding.

The user interface does not only visualize the spatial association but also the temporal association of the combined acquisitions.

While the measurement and/or image reconstruction of one or both modalities is being carried out, the user can advantageously already be conducting further planning. As soon as reconstructed data of at least one of both modalities is present, this data can be used to plan following measuring processes. In this case, the progress of the respective measuring processes (or reconstructions) is always visualized for the user.

Since the measurements of the two modalities can be imaged perfectly relative to one other, both the operational convenience for the user and the quality of the results data are thus increased in an advantageous manner.

The invention is not restricted by the disclosed example embodiments; rather, modifications and equivalent embodiments are possible within the scope of the invention, which is defined by the claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging objects using first and second imaging devices which differ at least in regard to at least one of spatial resolution and sensitivity, the method comprising:
    generating an overview image by at least one of the first and second imaging devices;
    simultaneously planning measurements of the first and second imaging devices based upon the generated overview image using a user interface, in which a common coordinate system for the first and second imaging devices is defined and the planning of the combined measurement is conducted in synchronized representation on the user interface, the planning measurements including setting parameters required for the first and second imaging devices, the setting parameters including at least one of,
    setting a field of view,
    setting a layer thickness and a layer spacing,
    setting a measurement volume, and
    setting weighting factors of the first or the second imaging device; and
    simultaneously conducting the planned measurements of the first and second imaging devices, thereby acquiring simultaneously an image data volume of the first imaging device and an image data volume of the second imaging device in the common coordinate system.

2. The method as claimed in claim 1, further comprising:
    superposing display of images recorded by the first imaging device and images recorded by the second imaging device.

3. The method as claimed in claim 2, wherein the first imaging device is a magnetic resonance tomography device (MR) or a computed tomography device (CT).

4. The method as claimed in claim 3, wherein the second imaging device is a single photon emission computed tomography device (SPECT) or a positron emission tomography device (PET).

5. The method as claimed in claim 2, wherein the second imaging device is a single photon emission computed tomography device (SPECT) or a positron emission tomography device (PET).

6. The method as claimed in claim 1, wherein the first imaging device is a magnetic resonance tomography device (MR) or a computed tomography device (CT).

7. The method as claimed in claim 1, wherein the second imaging device is a single photon emission computed tomography device (SPECT) or a positron emission tomography device (PET).

8. A device to conduct the method as claimed in claim 2.

9. A non-transitory computer readable medium including program segments for, when executed on a computer device, causing the computer device to implement the method of claim 1.

10. An apparatus for imaging objects using first and second imaging devices which differ at least in regard to at least one of spatial resolution and sensitivity, the apparatus comprising:
    a generator to generate an overview image by at least one of the first and second imaging devices;
    a first planner to simultaneously plan measurements of the first and second imaging devices based upon the generated overview image using a user interface, in which a common coordinate system for the first and second imaging devices is defined and the planning of the combined measurement is conducted in synchronized representation on the user interface, the first planner planning measurements including setting parameters required for the first and second imaging devices, the setting parameters including at least one of
    setting a field of view,
    setting a layer thickness and a layer spacing,
    setting a measurement volume, and
    setting weighting factors of the first or the second imaging device; and
    a conductor to simultaneously conduct the planned measurements of the first and second imaging devices, thereby acquiring simultaneously an image data volume of the first imaging device and an image data volume of the second imaging device in the common coordinate system.

11. The apparatus as claimed in claim 10, further comprising:
    a display to display a superposed display of images recorded by the first imaging device and images recorded by the second imaging device.

12. An apparatus for imaging objects using first and second imaging devices which differ at least in regard to at least one of spatial resolution and sensitivity, the apparatus comprising:
    a device to generate an overview image by at least one of the first and second imaging devices;
    a user interface to simultaneously plan measurements of the first and second imaging devices based upon the generated overview image, in which a common coordinate system for the first and second imaging devices is defined and the planning of the combined measurement is conducted in synchronized representation on the user interface, the user interface planning measurements includes setting parameters required for the first and second imaging devices, the setting parameters including at least one of, setting a field of view, setting a layer thickness and a layer spacing, setting a measurement volume, and setting weighting factors of the first or the second imaging device; and a display to simultaneously conduct the planned measurements of the first and second imaging devices, thereby acquiring simultaneously an image data volume of the first imaging device and an image data volume of the second imaging device in the common coordinate system.

13. The apparatus as claimed in claim 12, wherein the display is further useable to superpose display of images recorded by the first imaging device and images recorded by the second imaging device.

* * * * *